United States Patent [19]

Kawabe et al.

[11] Patent Number: 5,360,692
[45] Date of Patent: Nov. 1, 1994

[54] POSITIVE TYPE 1,2-NAPHTHOQUINONEDIAZIDE PHOTORESIST COMPOSITION CONTAINING BENZOTRIAZOLE LIGHT ABSORBING AGENT

[75] Inventors: Yasumasa Kawabe; Kazuya Uenishi; Tadayoshi Kokubo, all of Shizuoka, Japan

[73] Assignee: Fuji Photo Film Co., Ltd., Kanagawa, Japan

[21] Appl. No.: 70,795

[22] Filed: Jun. 3, 1993

[30] Foreign Application Priority Data

Jun. 4, 1992 [JP] Japan .................. 4-144395

[51] Int. Cl.$^5$ .................. G03F 7/023; G03C 1/61
[52] U.S. Cl. .................. 430/191; 430/192; 430/512
[58] Field of Search .................. 430/191, 512, 192

[56]  References Cited

U.S. PATENT DOCUMENTS

| | | | |
|---|---|---|---|
| 3,661,582 | 5/1972 | Broyde | 430/191 |
| 3,936,305 | 2/1976 | Hiraishi et al. | 430/512 |
| 4,681,905 | 7/1987 | Kubota et al. | 524/91 |
| 4,937,348 | 6/1990 | Kubota | 548/259 |
| 4,952,664 | 8/1990 | Masumoto et al. | 528/199 |
| 5,215,858 | 6/1993 | Koibuchi et al. | 430/191 |

*Primary Examiner*—Charles L. Bowers, Jr.
*Assistant Examiner*—Christopher G. Young
*Attorney, Agent, or Firm*—Sughrue, Mion, Zinn, Macpeak & Seas

[57] ABSTRACT

There is disclosed a positive type photoresist composition comprising an alkali-soluble resin, a compound having a 1,2-naphthoquinonediazido group, and at least one light absorbing agent selected from the group consisting of the compounds represented by the following formulae [I] and [II], the content of said light absorbing agent being in the range of 0.1 to 10% by weight based on the total solid content of the composition:

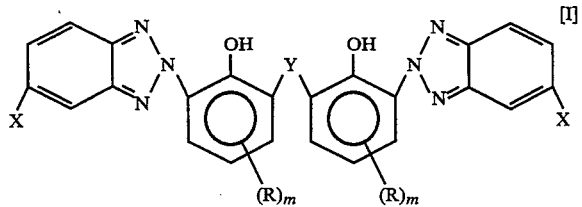

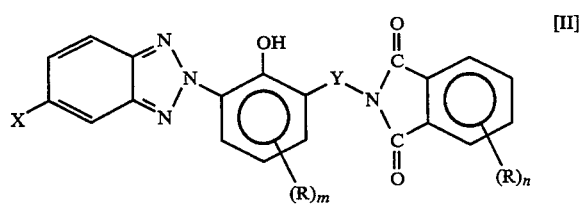

wherein X represents a hydrogen atom, a halogen atom, an alkyl group, an aralkyl group, an alkoxy group, an acyl group, or an aryl group; Y represents a single bond, an alkylene group, —O—, —S—, —SO$_2$—or

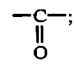

R represents a hydrogen atom, an alkyl group, or an aralkyl group; m represents an integer from 1 to 3; and n represents an integer from 1 to 4. The content of light absorbing agent in said composition is in the range of from 0.3% by weight to 5% by weight, based on the total solid content of the composition.

9 Claims, No Drawings

POSITIVE TYPE 1,2-NAPHTHOQUINONEDIAZIDE PHOTORESIST COMPOSITION CONTAINING BENZOTRIAZOLE LIGHT ABSORBING AGENT

FIELD OF THE INVENTION

The present invention relates to an improved positive type photoresist composition comprising an alkali-soluble resin and a 1,2-naphthoquinone diazido compound. More particularly, the present invention relates to a positive type photoresist composition which has excellent performances in forming fine patterns even on the surface of a substrate having unevenness or high reflectance.

The positive type photoresist composition according to the present invention is applied to a thickness of 0.5 to 3 μm on the surface of a substrate, such as semiconducting wafer, glass, ceramics or metal, using a spin coating method or a roller coating method. The coated material is then heated and dried. Thereafter, a pattern, such as a circuit pattern, is printed on the material through an exposure mask using irradiation with ultraviolet rays or the like. The material is then developed in order to obtain a positive image.

Subsequently, the positive image is used as a mask to effect patterned etching on a substrate. Typical applications of positive type photoresist include the production of semiconductors such as an IC, the production of circuit boards, such as liquid crystal and thermal head circuit boards, and in photofabrication.

BACKGROUND OF THE INVENTION

Positive type photoresist compositions are normally compositions comprising an alkali-soluble resin and a naphthoquinonediazide compound as a light-sensitive material. Examples of such compositions include novolak type phenol resin/naphthoquinone diazide-substituted compounds as disclosed in U.S. Pat. Nos. 3,666,473, 4,115,128, and 4,173,470. The most common examples of such compositions include a novolak resin made of cresol formaldehyde/trihydroxybenzophenone-1,2-naphthoquinone diazidosulfonic ester, as disclosed in L. F. Thompson, "Introduction to Microlithography", ACS, No. 219, pp. 112–121.

A novolak resin, which is a binder, can be dissolved in an aqueous alkaline solution without swelling. A novolak resin can also exhibit a high resistance, particularly to plasma etching, when an image thus produced is used as a mask for etching. Thus, a novolak resin is particularly useful in this application.

As a photosensitive material, a naphthoquinone diazide compound serves as a dissolution inhibitor in order to reduce the alkali solubility of the novolak resin. Such a compound is peculiar, however, in that it undergoes decomposition upon irradiation with light and produces an alkali-soluble substance which rather enhances the alkali solubility of the novolak resin. Because of the great change in properties resulting from irradiation with light, a naphthoquinone diazide compound is particularly useful as a photosensitive material for positive type photoresist.

From this standpoint, many positive type photoresists comprising a novolak resin and a naphthoquinone diazide photosensitive material have heretofore been developed and put to practical use. These positive type photoresists have attained sufficient results in working lines of a width of 1.5 to 2 μm.

However, even with the use of such positive type photoresists having a high resolution, if the patterns are formed on the surface of a substrate having a high reflectance, such as an aluminum substrate, a dim image is formed and it is very difficult to control the width of the lines which form the patterns, due to the influence of the light reflected by the surface of the substrate, which is known as halation. This phenomenon is more remarkable in the case where the substrate physically has different levels or steps.

For the purpose of solving such drawbacks, i.e., preventing halation, it has been known to incorporate a light absorbing material into the photoresist composition. For example, JP-B-51-37562 (the term "JP-B" as used herein means an "examined Japanese patent publication") describes a method in which the transmitting capability of the photoresist layer is reduced by incorporating therein a dye, Oil Yellow, having light absorption characteristics in the ultraviolet region, said dye being represented by the formula:

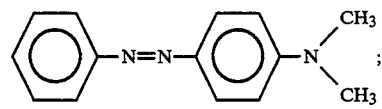

This results in the reduction of the amount of light which is reflected by the surface of the substrate and which passes through the photoresist layer, and thereby reduces the amount of light which is transmitted to the area that is not to be exposed to ultraviolet rays; whereby the resolution is prevented from being deteriorated.

However, when this dye is incorporated into the photoresist composition, a part of the light absorbing material present in the photoresist composition sublimes from the photoresist layer when a substrate coated with the photoresist composition solution is subjected to prebaking, which serves the purpose of removing the residual solvent in the coating and improving adhesion between the substrate and the coating. Consequently, the halation-preventing capability of the photoresist is considerably attenuated, and the resist performances, such as sensitivity or the like, become inconstant.

U.S. Pat. No. 4,287,289 describes derivatives of a light absorbing agent (1-alkoxy-4-(4'-N,N-dialkylaminophenylazo)benzene in which subliming characteristics during prebaking are improved. However, when such a light absorbing agent is incorporated into a common positive type photoresist composition, sensitivity is considerably attenuated.

JP-A-59-142538 (the term "JP-A" as used herein means an "unexamined punished Japanese patent application") describes an alkali-soluble azo compound. When this compound is used, the halation-preventing capability obtained is not fully satisfactory although the attenuation of sensitivity and the variability of sensitivity due to the nature of the light absorbing material used are low, and failing to meet the recent requirements of considerable miniaturization of working dimensions required in the semiconductor industry.

JP-A-1-241546 describes a system of a combination of an ultraviolet absorbing agent and a gallic acid ester or polyhydroxybenzophenone and a 1,2-naphthoquinone diazide and/or 1,2-naphthoquinone-4-sulfonic ester.

However, such a system does not provide a sufficient halation-preventing capability.

SUMMARY OF THE INVENTION

In view of the above, a general object of the present invention is to provide a positive type photoresist composition which can provide a resist pattern having an excellent dimensional stability, and in which the above-mentioned drawbacks of the conventional photosensitive compositions are overcome such that the requirements for the miniaturization of the working dimensions which are progressing rapidly in the production of semiconductor devices are met. A specific object of the present invention is to provide a positive type photoresist composition that can provide a resist pattern in which its resist performances are not rapidly reduced under prebaking conditions, and which has a high halation-preventing capability, and thus an excellent resolution.

The inventors have found that the above-mentioned objects of the present invention can be accomplished by incorporating a specific light absorbing agent into a positive type photosensitive resin composition containing a specific quinone diazide compound and an alkali-soluble novolak resin. Thus, the inventors have made the present invention based on the above finding.

More specifically, the objects of the present invention are accomplished with a positive type photoresist composition comprising an alkali-soluble resin, a compound having a 1,2-naphthoquinonediazido group, and at least one light absorbing agent selected from the group consisting of the compounds represented by the following formulae [I] and [II], such that at least one light absorbing agent is present in an amount of 0.1 to 10% by weight based on the total solid content in the positive type photoresist composition:

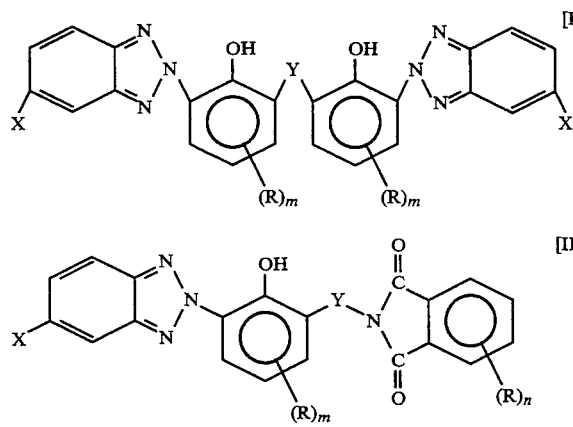

wherein X represents a hydrogen atom, a halogen atom, an alkyl group, an aralkyl group, an alkoxy group, an acyl group, or an aryl group; Y represents a single bond, an alkylene group, —O—, —S—, —SO$_2$—, or

R represents a hydrogen atom, an alkyl group, or an aralkyl group; m represents an integer from 1 to 3; and n represents an integer from 1 to 4.

DETAILED DESCRIPTION OF THE INVENTION

In formulae [I] and [II], the halogen atom represented by X is preferably a chlorine atom, a bromine atom, an iodine atom or a fluorine atom.

The alkyl group represented by X in formulae [I] and [II] is preferably a methyl, ethyl, propyl, isopropyl, n-butyl, isobutyl, sec-butyl, t-butyl, pentyl, isopentyl, t-pentyl, hexyl, isohexyl, heptyl, octyl, nonyl, decyl, undecyl group or the like.

The aralkyl group represented by X in formulae [I] and [II] is preferably a benzyl, α-methylbenzyl, cumyl group or the like.

The aryl group designated by X in formulae [I] and [II] is preferably a phenyl, xylyl, toluyl, cumenyl group or the like.

The alkoxy group designated by X in formulae [I] and [II] is preferably a methoxy, ethoxy, propoxy, isopropoxy group or the like.

The acyl group designated by X in formulae [I] an [II] is preferably an acetyl, butyryl, benzoyl, cyanamoyl group or the like.

All of the above mentioned groups may have a substituent group.

The alkylene group represented by Y in formulae [I] and [II] is preferably a methylene, ethylene, trimethylene, tetramethylene, pentamethylene, hexamethylene, heptamethylene, octamethylene, propylene group or the like.

The alkyl group and the aralkyl group represented by R in formulae [I] and [II] are preferably the same as the specific examples listed above, i.e., the alkyl group and the aralkyl group, respectively, with respect to X.

The compound represented by formula [I] can be obtained by, e.g., the methods described in JP-B-55-39180, JP-A-49-61071, JP-A-3-39329, and U.S. Pat. Nos. 4,681,905 and 4,937,348.

For instance, an example of such methods comprises subjecting a bisphenol compound represented by the following formula [III] and an o-nitrodiazonium salt to a coupling reaction to produce an azo compound, and then reducing and cyclizing the resulting azo compound:

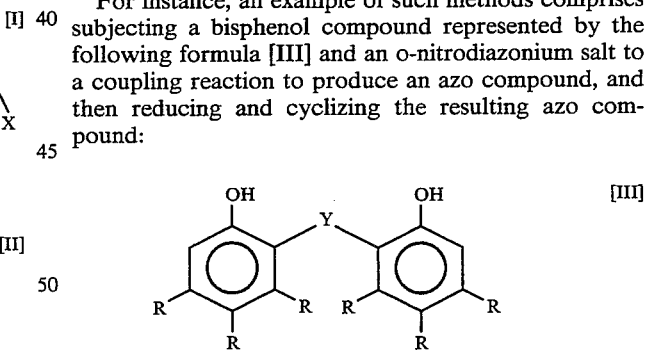

wherein Y and R represent the same substituents as those defined in formulae [I] and [II].

Another example of such methods comprises dimerizing a compound represented by the following formula [IV] in the presence of an acid with the use of an aldehyde or the like:

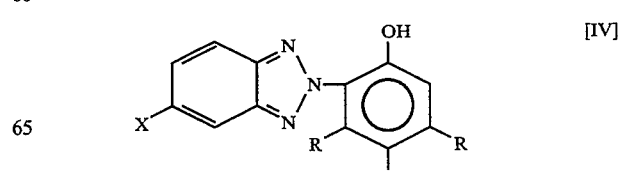

wherein X and R represent the same substituents as those defined in formulae [I] and [II].

Another example of such methods comprises reacting a compound represented by formula [III] with an amine and formaldehyde or the like to produce a Mannich base compound represented by the following formula [V], and then reacting the resulting Mannich base compound with a compound represented by formula [IV] or dimerizing the resulting Mannich base compound:

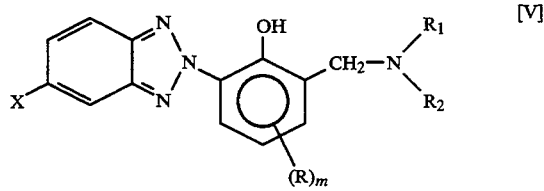

wherein X, R and m represent the same substituents as those defined in formula [I]; and $R_1$ and $R_2$ each represents a hydrogen atom or a lower alkyl group, or $R_1$ and $R_2$ may be such that they are bonded to each other to form a four-membered to six-membered ring in conjunction with a nitrogen atom, provided that when one of the $R_1$ and $R_2$ substituents is a hydrogen atom, the other is never a hydrogen atom.

Examples of the compound represented by formula [I] which can be used in the present invention include 2,2'-methylene-bis(4-methyl-6-benzotriazolylphenol) (light absorbing agent (1)), 2,2'-methylene-bis[4-(1,1,3,3-tetramethylbutyl)-6-benzotriazolylphenol] (light absorbing agent (2)), 2,2'-methylene-bis(4-cumyl-6-benzotriazolylphenol) (light absorbing agent (3)), 2,2'-octylidene-bis[4-methyl-6-(5'-chlorobenzotriazolyl)phenol] (light absorbing agent (4)), 2,2'-octylidenebis[4-methyl-6-(5'-methylbenzotriazolyl)phenol] (light absorbing agent (5)), and 2,2'-methylene-bis(4-tertoctyl-6-benzotriazolylphenol) (light absorbing agent (6)). In addition to the specific compounds listed, other appropriate compounds can also be used as the compound represented by formula [I] in the present invention.

The compound represented by formula [II] can be obtained by, e.g., the methods described in U.K. Patent 1,169,859 and U.S. Pat. Nos. 4,952,664 and 4,821,774.

An example of such methods comprises reacting a benzotriazole type compound having a phenolic hydroxyl group represented by formula [IV] with an alkylol phthalimide type compound represented by the following formula [VI]:

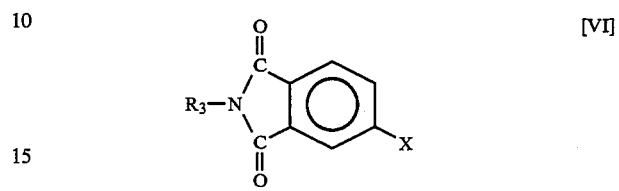

wherein X represents the same substituents as defined in formulae [I] and [II]; and $R_3$ represents a hydrogen atom, hydroxyl group, or a hydroxyalkyl group having a of from 1 to 4 carbon atoms.

Another example of such methods comprises allowing an amino group of a compound having an amino alkyl group on an aromatic ring having a phenolic hydroxyl group, such as 2-(2'-hydroxy-3'-aminoalkylphenyl)benzotriazole, and an acid anhydride group of phthalic anhydride or the like to undergo a dehydrocondensation reaction.

Examples of the compound represented by formula [II] which can be used in the present invention include 2-phthalimidomethyl-6-(2-benzotriazolyl) -4-methylphenol (light absorbing agent (7)), 2-phthalimidomethyl-6-(2-benzotriazolyl)-4-butylphenol (light absorbing agent (8)), 2-phthalimidoethyl-6-(2-benzotriazolyl) -4-ethylphenol (light absorbing agent (9)), and 2-phthalimidoethyl-6-(2-benzotriazolyl)4-tert-octylphenol (light absorbing agent (10)). In addition to the specific compounds listed, other appropriate compounds can also be used as the compound represented by formula [II] in the present invention.

Specific examples of the above mentioned light absorbing agents suitable for use in the present invention include:

Light absorbing agent (1)

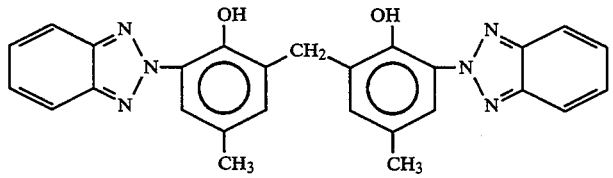

Light absorbing agent (2)

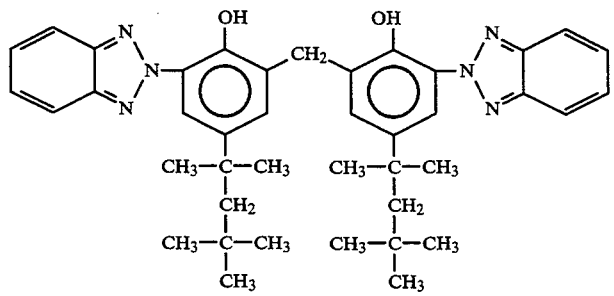

Light absorbing agent (3)

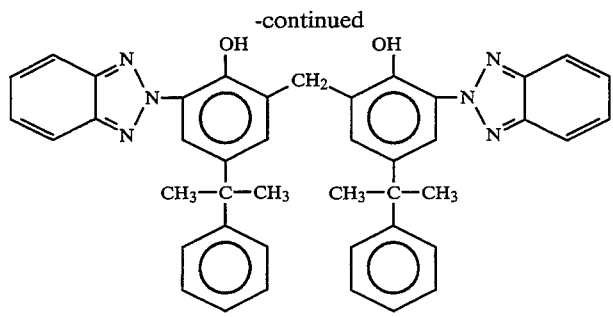
Light absorbing agent (4)
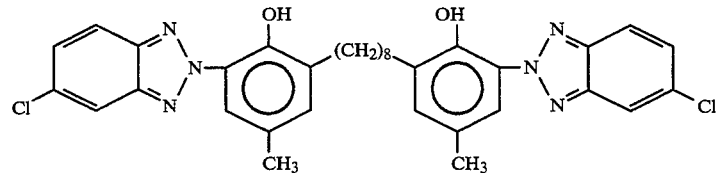
Light absorbing agent (5)
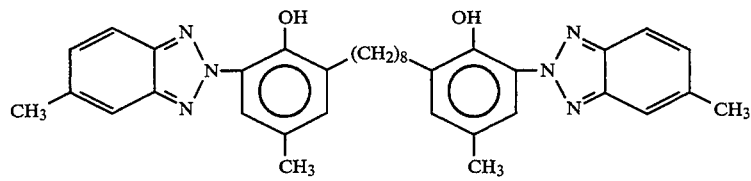
Light absorbing agent (6)
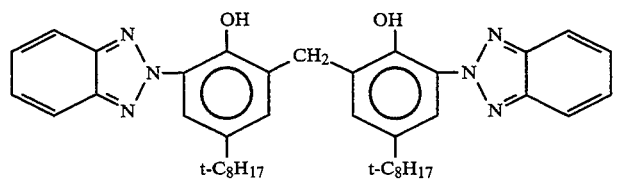
Light absorbing agent (7)
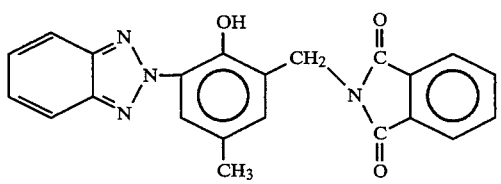
Light absorbing agent (8)
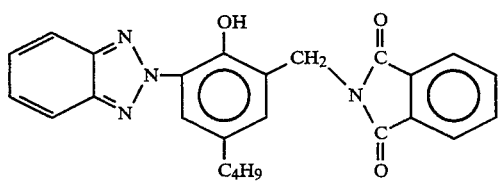
Light absorbing agent (9)
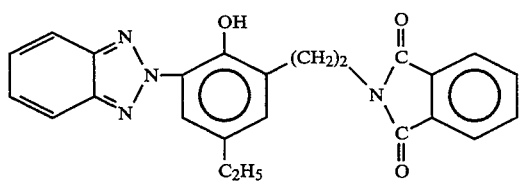
Light absorbing agent (10)

-continued

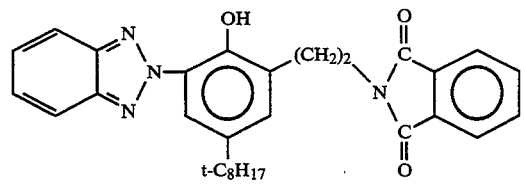

These compounds may be used alone, or in combination, in an amount of 0.1 to 10% by weight, preferably 0.3 to 5% by weight, based on the total solid content in the system. If the amount of light absorbing agent in the photoresist compound is less than the above mentioned range, a sufficient halation-preventing capability cannot be obtained. On the contrary, if the amount exceeds the above mentioned range, deposition occurs, giving disadvantageous results. The light absorbing agent of the present invention may be used in combination with a conventional light absorbing agent.

The conventional light absorbing agent may be used in an amount of about 50% by weight or less based on the amount of the light absorbing agent for use in the present invention and examples thereof are described for example in U.S. Pat. Nos. 4,828,960, 4,882,260, 4,983,492, 5,043,243 and 5,110,706 and European Patents 231522, 314037, 345714, 385442, 392409, 428398 and 455223.

Examples of the alkali-soluble resin to be used in the present invention include a novolak resin, an acetonepyrogallol resin, a polyhydroxy styrene, and derivatives of the polyhydroxy styrene.

Particularly preferred among these alkalisoluble resins is novolak resin. The novolak resin can be obtained by the addition condensation of an aldehyde with a predetermined monomer as a main component in the presence of an acidic catalyst.

Examples of such a predetermined monomer include: cresols, such as phenol, m-cresol, p-cresol and o-cresol; xylenols, such as 2,5-xylenol, 3,5-xylenol, 3,4-xylenol and 2,3-xylenol; alkylphenols, such as m-ethylphenol, p-ethylphenol, o-ethylphenol and p-t-butylphenol; trialkylphenols, such as 2,3,5-trimethylphenol, 2,3,4-trimethylphenol and 2,3,6-trimethylphenol; alkoxyphenols, such as p-methoxyphenol, m-methoxyphenol, 3,5-dimethoxyphenol, 2-methoxy-4-methylphenol, m-ethoxyphenol, p-ethoxyphenol, m-propoxyphenol, p-propoxyphenol, m-butoxyphenol and p-butoxyphenol; bisalkylphenols, such as 2-methyl-4-isopropylphenol; and hydroxyaromatic compounds, such as m-chlorophenol, p-chlorophenol, o-chlorophenol, dihydroxybiphenyl, bisphenol A, phenylphenol, resorcinol and naphthol. These monomers may be used alone, or in combination. The predetermined monomer which can be used in the present invention is not limited to these monomers.

Examples of the aldehydes used to make the novolak resin include formaldehyde, paraformaldehyde, acetaldehyde, propylaldehyde, benzaldehyde, phenylacetaldehyde, α-phenylpropylaldehyde, β-phenylpropylaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, p-nitrobenzaldehyde, p-methylbenzaldehyde, m-methylbenzaldehyde, p-methylbenzaldehyde, p-ethylbenzaldehyde, p-n-butylbenzaldehyde, furfural, chloroacetaldehyde, and acetal compounds thereof, e.g., chloroacetaldehyde diethyl acetal. Preferred among these aldehydes is formaldehyde.

These aldehydes may be used alone or in combination.

The acidic catalyst used to make the novolak resin can be hydrochloric acid, sulfuric acid, formic acid, acetic acid, or oxalic acid.

The weight-average molecular weight of the novolak resin thus obtained is preferably in the range of 2,000 to 30,000. If this value falls below 2,000, the reduction in the film on the unexposed portion after development is increased. On the contrary, if this value exceeds 30,000, the development speed is reduced. The particularly preferred range of the weight-average molecular weight of the novolak resin is from 6,000 to 20,000.

The weight-average molecular weight of the novolak resin is determined by gel permeation chromatography as calculated in terms of polystyrene.

The photosensitive material to be used in the present invention may comprise a product of esterification of a polyhydroxy compound as described below with 1,2-naphthoquinonediazido-5-(and/or -4-)sulfonyl chloride.

Examples of such a polyhydroxy compound include: polyhydroxyphenylalkylketones, such as 2,3,4-trihydroxyacetophenone, 2,3,4-trihydroxyphenylpentylketone and 2,3,4-trihydroxyphenylhexylketone; bis(-(poly)hydroxyphenyl)aklanes, such as bis(2,4-dihydroxyphenyl)methane, bis(2,3,4-trihydroxyphenyl)methane, bis(2,4-dihydroxyphenyl)propane-1, bis(2,3,4-trihydroxyphenyl)propane-1 and nordihydroguaiaretic acid; bis(polyhydroxybenzoyl)alkanes or bis(polyhydroxybenzoyl)aryls, such as bis(2,3,4-trihydroxybenzoyl)methane, bis(3-acetyl-4,5,6-trihydroxyphenyl)methane, bis(2,3,4-trihydroxybenzoyl)benzene and bis(2,4,6-trihydroxybenzoyl)benzene; alkylene di(-polyhydroxybenzoate)'s, such as ethylene glycol di(3,5-dihydroxybenzoate) and ethylene glycol di(3,4,5-trihydroxybenzoate); polyhydroxybiphenyls, such as 2,3,4-biphenyltriol, 3,4,5-biphenyltriol, 3,5,3',5'-biphenyltetrol, 2,4,2',4'-biphenyltetrol, 2,4,6,3',5'-biphenylpentol, 2,4,6,2',4',6'-biphenylhexol and 2,3,4,2',3',4'-biphenylhexol; bis(polyhydroxy)sulfides, such as 4,4'-thiobis(1,3-dihydroxy)benzene; bis(polyhydroxyphenyl)ethers, such as 2,2',4,4'-tetrahydroxydiphenyl ether; bis(-polyhydroxyphenyl)sulfoxides, such as 2,2',4,4'-tetrahydroxydiphenyl sulfoxide; bis(polyhydroxyphenyl)sulfones, such as 2,2',4,4'-diphenylsulfone; polyhydroxytriphenylmethanes, such as 4,4',3'',4'''-tetrahydroxy-3,5,3',5'-tetramethyltriphenylmethane, 4,4',2'',3'',4''-pentahydroxy-3,5,3',5'-tetramethyltriphenylmethane, 2,3,4,2',3',4'-hexahydroxy-5,5'-diacetyltriphenylmethane, 2,3,4,2',3',4',3'',4''-octahydroxy-5,5'-diacetyltriphenylmethane and 2,4,6,2',4',6'-hexahydroxy-5,5'-dipropionyltriphenylmethane; polyhydroxyspirobiindanes, such as 3,3,3',3'-tetramethyl-1,1'-spirobiindane-5,6,5',6'-tetrol, 3,3,3',3'-tetramethyl-1,1'-spirobiindane-5,6,7,5',6',7,-hexol, 3,3,3',3'-tetramethyl-1,1'-spirobiindane-4,5,6,4',5',6'-hexol and 3,3,3',3,-tetramethyl-1,1'-spirobiindane-4,5,6,5',6',7'-hexol; polyhydroxy phthalides, such as 3,3-bis(3,4-dihydroxyphenyl)phthalide, 3,3-bis(2,3,4-trihydroxyphenyl)phthalide and 3',4',5',6-tetrahydroxyspiro[phthalido-3,9'-xanthene]; polyhydroxybenzopyranes, such as 2-(3,4-dihydroxyphenyl)-3,5,7-trihydroxybenzopyrane, 2-(3,4,5-trihydroxyphenyl)-3,5,7-trihydroxybenzopyrane, 2-(3,4-dihydroxyphenyl)-3-(3,4,5-trihydroxybenzoyloxy)-5,7-dihydroxybenzopyrane and 2-(3,4,5-trihydroxyphenyl)-3-(3,4,5-trihydroxybenzoyloxy)-5,7-dihydroxybenzopyrane; and flavono dyes, such as morin, quercetin and rutin.

One product, or a combination of two or more products, of the esterification of these polyhydroxy compounds with naphthoquinone diazide can be used.

The amount of the photosensitive material to be used is in the range of 5 to 100 parts by weight, preferably 10 to 50 parts by weight, based on 100 parts by weight of alkali-soluble resin. If this value falls below 5 parts by weight, the percent film remaining is reduced. On the contrary, if this value exceeds 100 parts by weight, the sensitivity and the solubility of the photosensitive material in the solvent are reduced.

The composition of the present invention may further comprise other polyhydroxy compounds so that its solubility in the developer can be accelerated. Preferred examples of such polyhydroxy compounds include phenols, resorcin, phloroglucin, acetone-pyrogallol condensation resin, phloroglucide, 2,4,2',4'-biphenyltetrol, 4,4'-thiobis(1,3-dihydroxy)benzene, 2,2',4,4'-tetrahydroxydiphenylether, 2,2',4,4'-tetrahydroxydiphenylsulfoxide, and 2,2',4,4'-diphenylsulfone.

The content of the polyhydroxy compounds is 100 parts by weight or less, preferably 5 to 50 parts by weight, based on 100 parts by weight of the quinonediazide compound.

Examples of the solvent for dissolving the photosensitive material and the alkali-soluble novolak resin of the present invention include: ketones, such as methyl ethyl ketone and cyclohexanone; ketoethers, such as 4-ethyoxy-2-butanone and 4-methoxy-4-methyl-2-pentanone; alcohol ethers, such as ethylene glycol monomethyl ether and ethylene glycol monoethyl ether; ethers such as dioxane and ethylene glycol dimethyl ether; cellosolve esters, such as methyl cellosolve acetate and ethyl cellosolve acetate; fatty acid esters, such as butyl acetate, methyl lactate and ethyl lactate; halogenated hydrocarbons, such as 1,1,2-trichloroethylene; and high polarity solvents, such as dimethyl acetamide, N-methyl pyrrolidone, dimethyl formamide and dimethyl sulfoxide. These solvents may be used alone or in admixture.

The positive type photoresist composition of the present invention may comprise a surface active agent to further improve coating properties, such as striation.

Examples of such a surface active agent include: nonionic surface active agents, such as polyoxyethylene alkyl ethers (e.g., polyoxyethylene lauryl ether, polyoxyethylene stearyl ether, polyoxyethylene cetyl ether, polyoxyethylene oleyl ether), polyoxyethylene alkyl allyl ethers (e.g., polyoxyethylene octyl phenol ether, polyoxyethylene nonyl phenol ether), polyoxyethylenepolyoxypropylene block copolymers, sorbitan fatty acid esters (e.g., sorbitan monolaurate, sorbitan monopalmitate, sorbitan monostearate, sorbitan monooleate, sorbitan trioleate, sorbitan tristearate) and polyoxyethylene sorbitan fatty acid esters (e.g., polyoxyethylene sorbitan monolaurate, polyoxyethylene sorbitan monopalmitate, polyoxyethylene sorbitan monostearate, polyoxyethylene sorbitan trioleate, polyoxyethylene sorbitan tristearate); fluorine surface active agents, such as Eftop EF301, EF303 and EF352 (produced by Shin-Akita Kasei), Megafac F171, F173 (produced by Dainippon Ink And Chemicals, Incorporated), Fluorad FC430, FC431 (produced by Sumitomo 3M), and Asahi Guard AG710, Surflon S-382, SC101, SC102, SC103, SC104, SC105, SC106 (Asahi Glass Company, Limited); Organosiloxane polymer KP341 (produced by The Shin-Etsu chemical Industry Co., Ltd.); and acrylic or methacrylic (co)polymer Polyflow Nos. 75 and 95 (produced by Kyoeisha Yushi Kagaku Kogyo K.K.).

The amount of such a surface active agent to be blended in the system is normally in the range of 2 parts by weight or less, preferably 1 part by weight or less, based on 100 parts by weight of the alkali-soluble resin and quinone diazide compound in the composition of the present invention.

These surface active agents can be added to the system alone, or in combination.

A plasticizer and an adhesion aid may be incorporated into the positive type photoresist compound of the present invention, if desired. Examples of the plasticizer which can be used in the present invention include stearic acid, acetal resins, phenoxy resins and alkyd resins. Examples of the adhesion aid which can be used in the present invention include hexamethyldisilazanes and chloromethyl silanes.

The above mentioned positive type photoresist composition can be applied to the surface of a substrate for use in the preparation of precision integrated circuit elements (e.g., silicon/silicon dioxide coat) by a proper means, such as spinner and coater, exposed to light through a predetermined mask, and then developed to obtain an excellent resist. When the positive type photoresist composition of the present invention is used, an excellent resist can be obtained, even with a substrate having a high reflectance.

The developer for the positive type photoresist composition of the present invention can be an aqueous solution of an inorganic alkali, such as sodium hydroxide, potassium hydroxide, sodium carbonate, sodium silicate, sodium metasilicate and aqueous ammonia; a primary amine, such as ethylamine and n-propylamine; a secondary amine, such as diethylamine and di-n-butylamine; a tertiary amine, such as triethylamine and methyldiethylamine; an alcohol amine, such as dimethylethanolamine and triethanolamine; a quaternary ammonium salt, such as tetramethylammonium hydroxide and tetraethylammonium hydroxide; and a cyclic amine, such as pyrrole and piperidine. To such an aqueous solution of an alkali may be added an alcohol, a surface active agent or the like in a proper amount.

The present invention will be further described in the following examples, but the present invention should not be construed as being limited thereto. The percentage (%) indicates a value by weight unless otherwise specified.

EXAMPLE (1) Synthesis of novolak resin (a)

40 g of m-cresol, 60 g of p-cresol, 54.0 g of a 37% aqueous solution of formaldehyde and 0.05 g of oxalic acid were charged into a three-necked flask. The material was then heated to a temperature of 100° C. with stirring where it was allowed to undergo reaction for seven hours. After the reaction, the material was cooled to room temperature and its pressure was then reduced to 30 mmHg.

The reaction system was then gradually heated to a temperature of 150° C. to remove water and unreacted monomers therefrom. The novolak resin thus obtained exhibited an average molecular weight of 7,900 (as calculated in terms of polystyrene).

(2) Synthesis of novolak resin (b)

m-cresol and 3,5-dimethylphenol were condensed with the use of formaldehyde in the presence of oxalic acid as a catalyst in the same manner as in Synthesis Example (1) to obtain a novolak resin (a molar ratio of m-cresol to 3,5-dimethylphenole of 60/40). The resulting novolak resin exhibited an average molecular weight of 6,700.

(3) Synthesis of photosensitive material A 5.7 g of phloroglucin, 30.2 g of 1,2-naphthoquinonediazido-5-sulfonyl chloride and 300 ml of acetone were charged into a three-necked flask to make a uniform solution. The resulting solution was then allowed to react at a temperature of 25° C. for 3 hours with a mixture of 11.4 g of triethylamine and 50 ml of acetone gradually added dropwise thereto. The reaction mixture was then poured into 1,500 ml of a 1% aqueous solution of hydrochloric acid. The resulting precipitate was filtered off, washed with water, and then dried at a temperature of 40° C. to obtain 22.4 g of an ester of phloroglucin with 1,2-naphthoquinonediazido-5-sulfonic acid (photosensitive material A).

(4) Synthesis of photosensitive material B 11.7 g of 4,4'-thiobis(1,3-dihydroxy)benzene, 40.3 g of 1,2-naphthoquinonediazido-5-sulfonyl chloride and 300 ml of acetone were charged into a three-necked flask to make a uniform solution. The resulting solution was then allowed to react at a temperature of 25° C. for 3 hours with a mixture of 15.2 g of triethylamine and 50 ml of acetone gradually added dropwise thereto. The reaction mixture was then poured into 1,500 ml of a 1% aqueous solution of hydrochloric acid. The resulting precipitate was filtered off, washed with water, and then dried at a temperature of 40° C. to obtain 36.4 g of an ester of 4,4'-thiobis(1,3-dihydroxy)benzene with 1,2-naphthoquinonediazido-5-sulfonic acid (photosensitive material B).

(5) Synthesis of photosensitive material C 11.5 g of 2,3,4-trihydroxybenzophenone, 30.2 g of 1,2-naphthoquinonediazido-5-sulfonyl chloride and 300 ml of acetone were charged into a three-necked flask to make a uniform solution. The resulting solution was then allowed to react at a temperature of 25° C. for 3 hours with a mixture of 11.4 g of triethylamine and 50 ml of acetone gradually added dropwise thereto. The reaction mixture was then poured into 1,500 ml of a 1% aqueous solution of hydrochloric acid. The resulting precipitate was filtered off, washed with water, and then dried at a temperature of 40° C. to obtain 29.8 g of an ester of 2,3,4-trihydroxybenzophenone with 1,2-naphthoquinonediazido-5-sulfonic acid (photosensitive material C).

(6) Synthesis of photosensitive material D 12.3 g of 2,3,4,4'-tetrahydroxybenzophenone, 40.3 g of 1,2-naphthoquinonediazido-5-sulfonyl chloride and 300 ml of acetone were charged into a three-necked flask to make a uniform solution. The resulting solution was then allowed to react at a temperature of 25° C. for 3 hours with a mixture of 15.2 g of triethylamine and 50 ml of acetone gradually added dropwise thereto. The reaction mixture was then poured into 1,500 ml of a 1% aqueous solution of hydrochloric acid. The resulting precipitate was filtered off, washed with water, and then dried at a temperature of 40° C. to obtain 39.7 g of an ester of 2,3,4,4'-tetrahydroxybenzophenone with 1,2-naphthoquinonediazido-5-sulfonic acid (photosensitive material D).

(7) Synthesis of photosensitive material E 20.3 g of 3,4,5-trihydroxy propyl benzoate, 40.3 g of 1,2-naphthoquinonediazido-5-sulfonyl chloride and 300 ml of acetone were charged into a three-necked flask to make a uniform solution. The resulting solution was then allowed to react at a temperature of 25° C. for 3 hours with a mixture of 15.2 g of triethylamine and 50 ml of acetone gradually added dropwise thereto. The reaction mixture was then poured into 1,500 ml of a 1% aqueous solution of hydrochloric acid. The resulting precipitate was filtered off, washed with water, and then dried at a temperature of 40° C. to obtain 39.4 g of an ester of 3,4,5-trihydroxy propyl benzoate with 1,2-naphthoquinonediazido-5-sulfonic acid (photosensitive material E).

(8) Synthesis of Light Absorbing Agent (6): 2,2'-methylene-bis(4-tert-octyl-6-benzotriazolylphenol)

32.3 g of 2-benzotriazolyl-4-tert-octylphenol, 11.0 g of diethylamine and 5.2 g of paraformaldehyde were dissolved in 25 ml of butanol, and stirred for 24 hours under reflux.

Then, the solvent from the resulting solution was removed under reduced pressure to obtain 39.0 g of 2-diethylaminomethyl-4-tert-octyl-6-benzotriazolylphenol (a Mannich base compound).

37.0 g of the resulting product and 25.0 g of benzotriazolyl-4-tert-octylphenol were dissolved in 60 ml of xylene. To the resulting solution, 3.1 g of sodium methoxide (a 28% methanol solution) was added. The resulting mixture was stirred for 10 hours at reflux under nitrogen gas flow. From the resulting material was removed the solvent under reduced pressure to obtain 54.7 g of a crude product. The resulting crude product was recrystallized using n-heptane to obtain a white crystal having a melting point of 199° C. (the intended product).

(9) Synthesis of Light Absorbing Agent (1): 2,2'-methylene-bis(4-methyl-6-benzotriazolylphenol)

22.5 g of 4-methyl-6-benzotriazolylphenol, 11.0 g of diethylamine and 5.2 g of paraformaldehyde were dissolved in 25 ml of butanol, and heated to a temperature of 95° to 105° C. at which the solution was allowed to undergo reaction under reflux for about 24 hours. After the reaction, the solvent was removed from the reaction product under reduced pressure to obtain 30 g of 2-diethylaminomethyl-4-methyl-6-benzotriazolylphenol (a Mannich base compound).

7.8 g of the Mannich base compound was dissolved in 20 ml of xylene, to which 0.15 g of sodium methylate (a 28% methanol solution) was added as a catalyst. The resulting solution was then heated to a reflux temperature (140° to 150° C.) under a nitrogen gas flow and stirred for 10 hours. Thereafter, the solvent was removed from the reaction product under reduced pressure to obtain 6.1 g of a crude product. The resulting crude product was recrystallized using xylene to obtain a pale yellow crystal having a melting point of 284° C. (the intended product).

(10) Synthesis of Light Absorbing Agent (2): 2,2'-methylene-bis[4-(1,1,3,3-tetramethylbutyl)-6-benzotriazolylphenol]

37.0 g of 2-diethylaminomethyl-4-(1,1,3,3-tetramethylbutyl)-6-benzotriazolylphenol or a Mannich base compound, which had been obtained in the same manner as in Synthesis Example (9), except that 4-(1,1,3,3-tetramethylbutyl)-6-benzotriazolylphenol was used as the main material for the Mannich base compound, and 25.0 g of 4-(1,1,3,3-tetramethylbutyl)-6-benzotriazolylphenol were dissolved in 60 ml of xylene, to which 3.1 g of sodium methylate (a 28% methanol solution) was added as a catalyst. Then, the resulting solution was allowed to react in the same manner as in Synthesis Example (9). Thereafter, the solvent was removed from the reaction product under reduced pressure to obtain 55.1 g of a crude product. The resulting crude product was recrystallized using n-heptane to obtain a white crystal having a melting point of 200° C. (the intended product).

(11) Synthesis of Light Absorbing Agent (3): 2,2'-methylene-bis(4-cumyl-6-benzotriazolylphenol)

The xylene solution was prepared in the same manner as in Synthesis Example (10) except that there were used 10.0 g of 2-diethylaminomethyl-4-cumyl-6-benzotriazolylphenol or a Mannich base compound, which had been obtained in the same manner as in Synthesis Example (10), except that 4-cumyl-6-benzotriazolylphenol was used as the main material for the Mannich base compound, and 6.6 g of 4-cumyl-6-benzotriazolylphenol. The resulting solution was allowed to react in the same manner as in Synthesis Example (10) and subjected to the same treatment as in Synthesis Example (10) to obtain an opal crystal having a melting point of 191° C. (the intended product).

(12) Synthesis of Light Absorbing Agent (5): 2,2'-octylidene-bis[4-methyl-6-(5'-methylbenzotriazolyl)-phenol]

Dry hydrogen chloride was introduced into a benzene solution, which contains 129.6 g of p-cresol, 64.1 g of n-caprylaldehyde and 2 ml of n-dodecyl mercaptan, at room temperature in 4 hours.

The resulting mixture was allowed to stand overnight at room temperature. Thereafter, the reaction mixture was washed with water, then with a 1N aqueous sodium bicarbonate solution until the mixture exhibited weak acid, and then again with water. The solvent was removed from the resulting material by means of distillation after drying the benzene layer. The resulting residue was subjected to distillation under reduced pressure, followed by recrystallization using n-heptane to obtain a white crystal of 2,2'-octylidene-bis(4-methylphenol) having a melting point of 108° C.

To 60.8 g of 4-methyl-2-nitroaniline, 120 ml of concentrated hydrochloric acid and 40 ml of water were added with thorough stirring. To the resulting mixture was dropwise added the solution, which comprised 28.9 g of sodium nitrite dissolved in 50 ml of water, at a temperature of 0° C. in 10 minutes. After an additional 2-hours of stirring, to the resulting mixture was added a small amount of sulfamic acid. The impurities were filtered out of the resulting material to obtain a diazonium solution of 4-methyl-2-nitroaniline.

32.6 g of the 2,2'-octylidene-bis(4-methylphenol) obtained above was dissolved in a mixed solution of 50 g of sodium hydroxide in 300 ml methanol and 200 ml of acetone, to which the diazonium solution of 4-methyl-2-nitroaniline obtained above was added dropwise with stirring at an inner temperature range of 0° to 10° C. After an additional 2-hour of stirring, to the reaction mixture was added glacial acetic acid so that the pH value of the mixture was 4 to 5. The resulting oily product was washed with methanol to obtain 2,2'-octylidene-bis[4-methyl-6-(4''-methyl-2''-nitrophenylazo)-phenol].

6.5 g of the azophenol thus obtained was suspended in 100 ml of ethanol and heated to a reflux temperature. To the resulting suspension was added 50 ml of water containing 8.4 g of sodium hydroxide, to which 6.5 g of zinc dust was gradually added. After an additional 1-hour of reflux, the zinc dust was filtered out at that temperature, and the pH value of the filtrate was made 4 to 5 with 1N hydrochloric acid. Then, the resulting deposit was collected by filtration, and recrystallized using methanol to obtain a white crystal having a melting point of 145° C. (the intended product).

(13) Synthesis of Light Absorbing Agent (7): 2-phthalimidomethyl-6-(2-benzotriazolyl)-4-methylphenol 500.0 g of 2-(2'-hydroxy-3'-aminomethyl-5'-methylphenyl) benzotriazole and 290.0 g of phthalic anhydride were mixed with each other. Then, the mixture was melted at a temperature of 170° to 180° C. and stirred for about one hour to undergo reaction. After cooling, the reaction product was introduced into 3 l of boiled methanol, subjected to filtration and allowed to stand overnight at room temperature, so that there was obtained 500.0 g of a pale yellow crystal having a melting point of 159° C. (the intended product).

(14) Synthesis of Light Absorbing Agent (8): 2-phthalimidomethyl-6-(2-benzotriazolyl)-4-butylphenol The intended product was obtained in the same manner as in Synthesis Example (13), except that 590.0 g of 2-(2'-hydroxy-3'-aminomethyl-5'-butylphenyl)benzotriazole was used in place of 500.0 g of 2-(2'-hydroxy-3'-aminomethyl-5'-methylphenyl)benzotriazole.

EXAMPLES 1 TO 13

Preparation of Positive Type Photoresist Compositions

A novolak resin selected from the group consisting of novolak resin (a) and novolak resin (b) obtained in Synthesis Examples (1) and (2), respectively; a photosensitive material selected from the group consisting of photosensitive materials A, B, C, D and E obtained in Synthesis Examples 3 to 7, respectively; and a light absorbing agent according to the present invention were dissolved in 18.0 g of ethyl lactate in the proportions set forth in Table 1. The resulting solution was filtered through a microfilter having a pore diameter of 0.2 μm to obtain a photoresist composition. Then, the resulting photoresist composition was applied to the surface of a silicon wafer with an aluminum film thereon by a spinner, and then dried by a vacuum hot plate at a temperature of 90° C. for 60 seconds to obtain a photoresist film having a thickness of 1.5 μm.

The photoresist film was exposed to light through a test chart mask by means of a reduction projection exposing apparatus LD-5010, available from Hitachi Seisakusho, developed with a 2.38% aqueous tetramethyl ammonium hydroxide solution for 1 minute, washed with water for 30 seconds, and then dried to obtain a resist pattern.

TABLE 1

| Example | Novolak resin | | Photosensitive material | | Light absorbing agent | |
|---|---|---|---|---|---|---|
| | Type | Weight (g) | Type | Weight (g) | Type | Weight (g) |
| 1 | a | 5.0 | A | 1.2 | 3 | 0.18 |

TABLE 1-continued

| Example | Novolak resin Type | Novolak resin Weight (g) | Photosensitive material Type | Photosensitive material Weight (g) | Light absorbing agent Type | Light absorbing agent Weight (g) |
| --- | --- | --- | --- | --- | --- | --- |
| 2 | a | 5.0 | B | 1.2 | 2 | 0.16 |
| 3 | a | 5.0 | D | 1.2 | 6 | 0.18 |
| 4 | a | 5.0 | E | 1.2 | 7 | 0.16 |
| 5 | a | 5.0 | C | 1.2 | 6 | 0.16 |
| 6 | a | 5.0 | D | 1.2 | 5 | 0.18 |
| 7 | b | 5.0 | A | 1.2 | 1 | 0.16 |
| 8 | b | 5.0 | B | 1.2 | 7 | 0.16 |
| 9 | b | 5.0 | C | 1.2 | 2 | 0.16 |
| 10 | b | 5.0 | D | 1.2 | 3 | 0.18 |
| 11 | b | 5.0 | C | 1.2 | 6 | 0.16 |
| 12 | b | 5.0 | D | 1.2 | 6 | 0.16 |
| 13 | b | 5.0 | E | 1.2 | 5 | 0.16 |

COMPARATIVE EXAMPLES 1 TO 5

A novolak resin selected from the group consisting of novolak resin (a) and novolak rein (b) obtained in Synthesis Examples (1) and (2), respectively; a photosensitive material selected from the group consisting of photosensitive materials A, B, C, D and E obtained in Synthesis Examples 3 to 7, respectively; and a light absorbing agent listed in Table 2 were dissolved in 18.0 g of ethyl lactate in the proportions set forth in Table 2. Then, a resist pattern was obtained in the same manner as in Examples 1 to 13.

TABLE 2

| Comparative Example | Novolak Resin Type | Novolak Resin Weight (g) | Photosensitive Material Type | Photosensitive Material Weight (g) | Light Absorbing Agent Type | Light Absorbing Agent Weight (g) |
| --- | --- | --- | --- | --- | --- | --- |
| 1 | a | 5.0 | A | 1.2 | none | — |
| 2 | a | 5.0 | D | 1.2 | Oil Yellow (2-dimethyl-aminoazobenzene) | 0.18 |
| 3 | b | 5.0 | C | 1.2 | 2-(2'-hydroxy-5'-methyl-phenyl)-benzotriazole | 0.16 |
| 4 | b | 5.0 | B | 1.2 | 2,4-hydroxy-azobenzene | 0.16 |
| 5 | b | 5.0 | E | 1.2 | 2-(2'-hydroxy-3',5'-di-t-butyl-phenyl)-benzotriazole | 0.16 |

Evaluation of Resist Patterns

The resist patterns obtained in the Examples 1 to 13, and Comparative Examples 1 to 5 were observed under a scanning electron microscope for evaluation of the performances of the photoresist compositions. The results are shown in Table 3.

TABLE 3

| | Relative Sensitivity | Resolving power (μm) | Anti-sublimation properties | Halation-preventing capability*1 | Depositing characteristics*2 |
| --- | --- | --- | --- | --- | --- |
| Example 1 | 0.9 | 0.50 | 0.99 | A | ○ |
| Example 2 | 1.1 | 0.50 | 0.99 | A | ○ |
| Example 3 | 1.1 | 0.50 | 0.99 | A | ○ |
| Example 4 | 1.4 | 0.50 | 0.99 | A | ○ |
| Example 5 | 1.2 | 0.50 | 0.99 | A | ○ |
| Example 6 | 1.1 | 0.50 | 0.99 | A | ○ |
| Example 7 | 1.1 | 0.50 | 0.99 | A | ○ |
| Example 8 | 1.3 | 0.50 | 0.99 | A | ○ |
| Example 9 | 1.1 | 0.50 | 0.99 | A | ○ |
| Example 10 | 1.1 | 0.50 | 0.99 | A | ○ |
| Example 11 | 1.2 | 0.50 | 0.99 | A | ○ |
| Example 12 | 1.1 | 0.50 | 0.99 | A | ○ |
| Example 13 | 1.1 | 0.50 | 0.99 | A | ○ |
| Comparative Example 1 | 1.0 | 0.55 | — | C | — |
| Comparative Example 2 | 4.5 | 0.60 | 0.82 | B | ○ |
| Comparative Example 3 | 1.2 | 0.50 | 0.99 | B | ○ |
| Comparative Example 4 | 1.5 | 0.60 | 0.97 | B | X |
| Comparative Example 5 | 1.9 | 0.60 | 0.98 | B | ○ |

*1 A: good
B: acceptable
C: nonacceptable
*2 Deposition of the particular light absorbing agent after left to stand at a temperature of 40° C. for 30 days.
○: no deposition
X: deposition observed The sensitivity is defined as the reciprocal of the exposure reproducing a 1.0 μm mask pattern, and as shown in Table 3, expressed in terms of a relative value with respect to the sensitivity of the product obtained in Comparative Example 1.

The resolving power is shown in Table 3, expressed in terms of a threshold resolving power at the exposure reproducing a 1.0 μm mask pattern.

The photoresist compositions having antisublimation properties were applied to the surface of glass wafers. The absorbance of each of the resulting products at 365 nm was measured with a spectrophotometer before and after the glass wafer was prebaked in a convection oven at 90° C. for 30 minutes. The antisublimation properties are shown in Table 3, expressed in terms of a ratio of the absorbance value measured after the prebaking to the absorbance value measured before the prebaking.

The halation-preventing capability is shown in Table 3, expressed in terms of the appearance of the surface of each test sample on which the pattern is formed, as observed under the electron microscope.

The results shown in Table 3 demonstrate that the positive type photoresist compositions according to the present invention provided excellent sensitivity, resolving power, anti-sublimation properties and halation-preventing capability.

In addition, Table 3 shows that the solutions for the positive type photoresist compositions according to the present invention did not demonstrate any depositing of the light absorbing agents after the solutions were left to stand at a temperature of 40° C. for 30 days.

The positive type photoresist composition of the present invention can provide a photoresist which has an excellent controlability of the width of the lines forming the patterns thereof, even on a substrate having a high reflectance, and which has various excellent properties, such as high sensitivity, high resolving power, good anti-sublimation properties, good halation-preventing capability and the like. Thus, the positive type photoresist composition of the present invention is suitable for use as a photoresist for fine working.

While the invention has been described in detail and with reference to specific embodiments thereof, it will be apparent to one skilled in the art that various changes and modifications can be made therein without departing from the spirit and scope thereof.

What is claimed is:

1. A positive type photoresist composition comprising, in admixture, an alkali-soluble resin, a compound having a 1,2-naphthoquinonediazido group, and at least one light absorbing agent selected from the group consisting of the compounds represented by formulae (I) and (II):

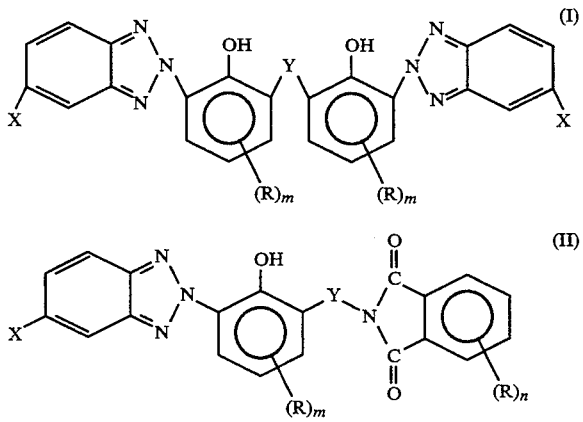

wherein X represents a hydrogen atom, a halogen atom, an alkyl group, an aralkyl group, an alkoxy group, an acyl group, or an aryl group; Y represents a single bond, an alkylene group, —O—, —S—, —SO$_2$—or

R represents a hydrogen atom, an alkyl group, or an aralkyl group; m represents an integer of from 1 to 3; and n represents an integer of from 1 to 4; and wherein the amount of said light absorbing agent is in a range of from 0.1 to 10% by weight based on the total solid content of the composition, and the compound having a 1,2-naphthoquinonediazido group is present in a range of from 5 to 100 parts by weight, based on 100 parts by weight of the alkali-soluble resin.

2. The positive type photoresist composition according to claim 1, wherein the content of light absorbing agent in said composition is in the range of from 0.3% by weight to 5% by weight, based on the total solid content of the composition.

3. The positive type photoresist composition according to claim 1, wherein the light absorbing agent in said composition is a compound represented by formula (I).

4. The positive type photoresist composition according to claim 1, wherein the light absorbing agent in said composition is a compound represented by formula (II).

5. The positive type photoresist composition according to claim 1, wherein the alkali-soluble resin of said photoresist composition is selected from the group consisting of a novolak resin, an acetonepyrogallol resin, a polyhydroxy styrene, and derivatives of the polyhydroxy styrene.

6. The positive type photoresist composition according to claim 5, wherein the alkali-soluble resin of said photoresist is a novolak resin.

7. The positive type photoresist composition according to claim 6, wherein said novolak resin has a weight-average molecular weight of from 2,000 to 30,000.

8. The positive type photoresist composition according to claim 7, wherein said novolak resin has a weight-average molecular weight of from 6,000 to 20,000.

9. The positive type photoresist composition according to claim 1, wherein the amount of the compound having a 1,2-naphthoquinonediazido group is 10 to 50 parts by weight, based on 100 parts by weight of the alkali-soluble resin.

* * * * *